(12) United States Patent
Bicker et al.

(10) Patent No.: US 9,415,346 B2
(45) Date of Patent: Aug. 16, 2016

(54) PROCESS FOR THE RECOVERY OF BETAINES FROM ELECTRODIALYSIS WASTE STREAM

(75) Inventors: Markus Bicker, Liederbach (DE); Miguel Angel Caraucán Dávila, Birgisch (CH)

(73) Assignee: Lonza Ltd., Visp (CH)

( * ) Notice: Subject to any disclaimer, the term of this patent is extended or adjusted under 35 U.S.C. 154(b) by 1062 days.

(21) Appl. No.: 13/147,902

(22) PCT Filed: Feb. 3, 2010

(86) PCT No.: PCT/EP2010/000655
§ 371 (c)(1),
(2), (4) Date: Oct. 20, 2011

(87) PCT Pub. No.: WO2010/089095
PCT Pub. Date: Aug. 12, 2010

(65) Prior Publication Data
US 2012/0035394 A1    Feb. 9, 2012

Related U.S. Application Data

(60) Provisional application No. 61/149,893, filed on Feb. 4, 2009.

(30) Foreign Application Priority Data

Feb. 4, 2009    (EP) .................................. 09001502

(51) Int. Cl.
*B01D 61/58*    (2006.01)
*B01D 61/42*    (2006.01)
*B01D 61/44*    (2006.01)
*C02F 1/44*    (2006.01)
(Continued)

(52) U.S. Cl.
CPC .............. *B01D 61/58* (2013.01); *B01D 61/422* (2013.01); *B01D 61/44* (2013.01); *C02F 1/44* (2013.01); *C02F 1/4693* (2013.01); *C07C 227/40* (2013.01); *C13B 20/165* (2013.01); *C13B 20/18* (2013.01); *B01D 61/02* (2013.01); *B01D 61/025* (2013.01); *B01D 61/027* (2013.01); *B01D 61/145* (2013.01); *B01D 61/147* (2013.01); *C02F 1/441* (2013.01); *C02F 1/442* (2013.01); *C02F 1/444* (2013.01); *C02F 2103/36* (2013.01)

(58) Field of Classification Search
CPC ............................. B01D 61/58; B01D 61/422
See application file for complete search history.

(56) References Cited

U.S. PATENT DOCUMENTS 4,708,936 A * 11/1987 Kulla et al. ................... 435/128
6,030,535 A    2/2000 Hayashi et al.

FOREIGN PATENT DOCUMENTS

DE    19634640 A1    3/1998
EP    0163222 A1    12/1985
(Continued)

OTHER PUBLICATIONS

Strathmann, H. Membrane Science and Technology 2004, 9, 1-22.*
(Continued)

*Primary Examiner* — Matthew Coughlin
(74) *Attorney, Agent, or Firm* — Dority & Manning, PA

(57) ABSTRACT

The present invention discloses a process for the recovery of betaines from electrodialysis (ED) waste streams, whereby said waste streams are treated with a pressure driven membrane process.

15 Claims, 2 Drawing Sheets

(51) Int. Cl.
*C02F 1/469* (2006.01)
*C07C 227/40* (2006.01)
*C13B 20/16* (2011.01)
*C13B 20/18* (2011.01)
*B01D 61/02* (2006.01)
*B01D 61/14* (2006.01)
*C02F 103/36* (2006.01)

(56) References Cited

FOREIGN PATENT DOCUMENTS

| EP | 0349297 | A1 | 1/1990 |
| WO | 2004013048 | A2 | 2/2004 |
| WO | 2008074042 | A2 | 6/2008 |

OTHER PUBLICATIONS

Somicon, Nitto Standard Spiral Wound Membrane List, Jan. 2007.*
Yu et al. Desalination 2001, 140, 97-100.*
Schaep et al. Chemistry for the Protection of the Environment, Chapter 14: Retention Mechanisms in Nanofiltration, 1998, pp. 117-125.*
Bellona et al. Water Research 2004, 38, 2795-2809.*
Boussu et al. Desalination 2006, 191, 245-253.*
Artug, G. Modeling and Simulation of Nanofiltration Membranes, Cuvillier Verlag, 2007, p. 9.*

* cited by examiner

PROCESS FOR THE RECOVERY OF BETAINES FROM ELECTRODIALYSIS WASTE STREAM

This application is the U.S. National Phase of, and Applicants claim priority from, International Patent Application Number PCT/EP2010/000655 filed Feb. 3, 2010, U.S. Provisional Patent Application bearing Ser. No. 61/149,893 filed Feb. 4, 2009, and European Patent Application bearing Serial Number 09001502.5 filed Feb. 4, 2009.

BACKGROUND OF THE INVENTION

The present invention discloses a process to recover betaines from electrodialysis waste streams from betaine production processes by pressure driven membrane processes.

The synthesis of betaines very often goes along with the production of stoichiometric amounts of organic or inorganic salts in the reaction mixture. Usually the products are further separated from the salts by various purification methods such as distillation, extraction, crystallization, electrodialysis or other unit operations. Every purification/separation process inevitably suffers from product losses.

Electrodialysis (ED) is a membrane technology used to purify organic products in liquid mixtures. The ED can be used to reduce the salt concentration in a mixture in a discretionary way and furthermore for the selective removing of organic compounds contained in a liquid solution. The driving force for this separation is an electric field over the membranes. Due to diffusion phenomena and/or osmotic pressure, product losses into the waste stream are inevitable. (see EP 0163222 B2, example 1c, disclosing a yield of 82%)

Pressure driven membrane processes such as Reverse Osmosis, nanofiltration, ultrafiltration or microfiltration can be applied to concentrate/retain organic compounds. The salts will only be partially concentrated/retained, depending on the type of membrane used.

The present state of the art suffers from several major disadvantages. The product losses in the waste stream due to e.g. diffusion and/or osmotic pressure decrease the yield of the ED process and contribute to the organic freight (total organic carbon, TOC) of the waste stream. Consequently, the waste stream can frequently not be properly treated in a biological waste stream treatment plant if the product is poorly biodegradable, requiring a subsequent incineration step with prohibitive costs for the industrial production. Thus, there is a need for a novel method for the minimization of product losses during the purification of betaine compounds.

SUMMARY OF THE INVENTION

The drawbacks of the state of the art outlined above can be overcome by the process according to the present invention, whereby ED waste streams are treated with a pressure driven membrane process and the recovered betaines are returned into the ED unit to improve the yields.

DETAILED DESCRIPTION OF THE INVENTION

Figure 1:
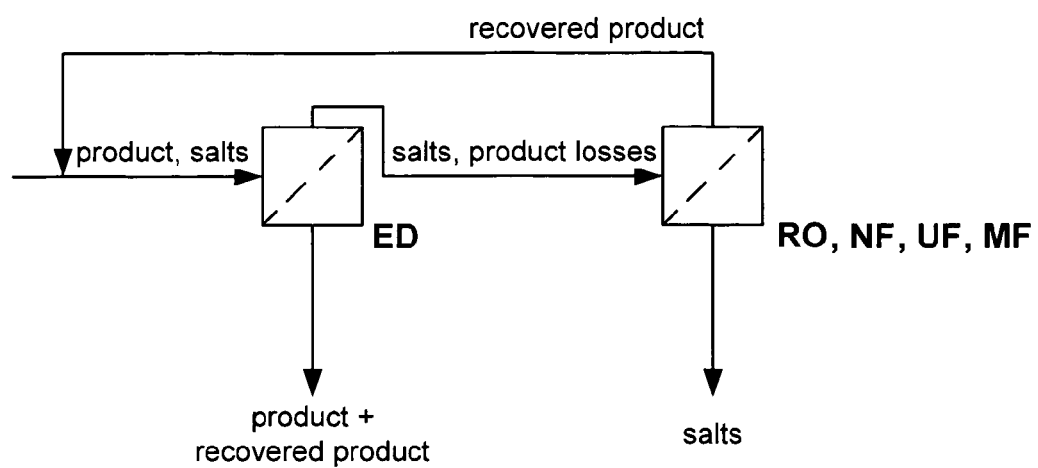
FIG. 1 depicts the process according to the invention with one ED and one recovery unit.

The production of betaines according to the invention such as 4-butyrobetain and L-carnitine comprises their purification using ED. The operating parameters of the ED are controlled in such a way as to achieve two goals simultaneously during this purification step. The first one consists in the reduction of inorganic salts like sodium chloride (NaCl), sodium hydroxide (NaOH), tetramethylammonium, etc. present in the liquid solutions of the betaines. The second goal consists in the selective removing of organic compounds like 4-hydroxybutanoic acid, (E)-4-Hydroxycrotonic acid, trimethylamine, etc. The ED parameters to be adjusted in each ED stream (feed, diluate, concentrate and electrolyte) in order to achieve these goals are pH, concentration of salts and organic compounds, electrical conductivity, temperature, etc. Said adjustment is within the routine capability of the skilled person. The applied membranes for the ED should allow a high grade of desalting and removing of undesirable organic compounds like 4-hydroxybutanoic acid or (E)-4-Hydroxycrotonic acid and should at the same time minimize losses of betaine compounds into the concentrate stream of the ED.

The applied membranes for the pressure driven processes such as Reverse Osmosis, nanofiltration, ultrafiltration or microfiltration should retain the desired betaines to the highest degree possible, whereas the retention of the salts and undesirable organic compounds like 4-hydroxybutanoic acid or (E)-4-Hydroxycrotonic acid should be minimized. Due to the similarities of the structure of the betaine compounds (e.g. 4-butyrobetain and L-carnitine) with the respective organic compounds (e.g. 4-hydroxybutanoic acid and (E)-4-Hydroxycrotonic acid), it is surprising that a good retention grade for the betaine compounds and a substantially reduced grade of retention for the organic compounds, respectively can be achieved by the process according to the invention. This difference in the retention grade of the compounds of a mixture allows their separation.

The grade of retention of betaines like 4-butyrobetain and L-carnitine and their impurities like 4-hydroxybutanoic acid and (E)-4-Hydroxycrotonic acid, respectively, can be controlled adjusting the operating parameters: temperature, pressure, flux, filtration cycles and concentration factor during the filtration process. Again, said adjustments are within the routine capability of the skilled person.

Thus, the retention grade achieved for the betaines is preferably between 1-100%, more preferably between 50-100%, even more preferably between 80-100% and most preferably 100%. Meanwhile, the retention grade achieved for the organic impurities is preferably between 30-95%. The process according to the invention allows for a great degree of flexibility with regards to separating the impurities present in the mixture of betaines. The adjustment of the filtration parameter mentioned above will determine whether a high grade of separation is achieved. It can become a key benefit in order to achieve a significant reduction of the organic freight (total organic carbon, TOC) of the waste stream of the ED and in order to avoid an accumulation of impurities like 4-hydroxybutanoic acid and (E)-4-Hydroxycrotonic due to the recycling of some ED streams inside the purification process.

According to the invention, the retention grade of the salts is preferably below 100%, more preferably in the range of 0-50% and most preferably 0-10%.

The membranes according to the present invention are those which are routinely used in the field. Specifically, they include polymeric membranes, ceramic membranes and special organic solvent stable polymeric membranes in case the ED waste stream contains organic solvents like alcohols, ketones, esters, ethers, aromatic or chlorinated solvents. Preferably, the pressure driven membrane process is reverse osmosis, nanofiltration, ultrafiltration or microfiltration.

The desired products according to the invention are betaines.

Preferably, said betaines are selected from the group consisting of 4-butyrobetain and L-carnitine.

The products according to the invention preferably have a good solubility in water.

Figure 2:
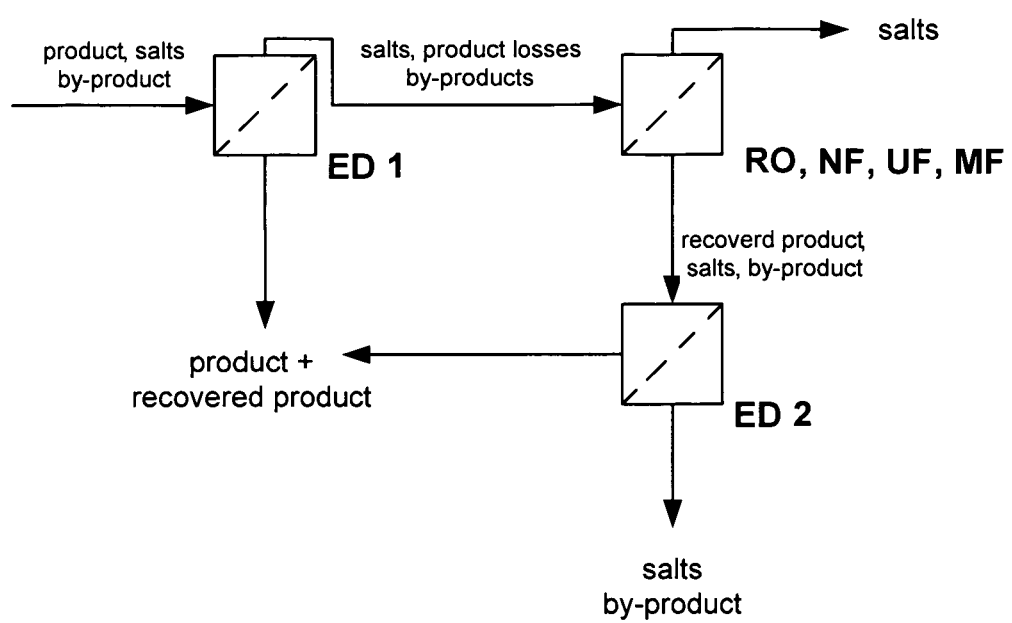
FIG. 2 depicts the process according to the invention with two ED and one recovery unit.

The present invention also contemplates a process whereby the ED waste streams are treated with a pressure driven membrane process and subsequently channelled into a second ED unit as depicted in FIG. 2 to improve the yield of the betaines The present invention achieves a remarkable yield increase in the purification of betaine products like 4-butyrobetain and L-carnitine using ED and at the same time a substantial reduction of the organic freight (total organic carbon, TOC) of the waste stream of the ED. Both aspects are economically significant for the competitiveness of the production of betaines like 4-butyrobetain and L-carnitine.

EXAMPLES

The present invention will be described in more detail in the following examples.

Comparative Example

Setup and Description of ED Experiments on Miniplant Scale

The setup used to carry out the ED treatments consisted of an ED miniplant equipped with a stack with 10 pairs of PES-Membranes of 64 $cm^2$. The experiments were carried out in batch-mode; however, a continuous operation mode can be also implemented. 3 pumps were responsible to circulate the concentrate (waste water stream), dilute (product stream) and electrolyte (service stream) solutions to the membrane stack. The flux of these 3 streams were adjusted and measured with 3 rotameters.

In order to guarantee a selective removal of the side-products during the ED-treatment and hence a maximisation of the process yield, a control of pH and temperature in the concentrate and dilute streams was implemented. During the ED-experiments pH, electrical conductivity, temperature and flux of these 3 streams are controlled and recorded.

The above described setup was used to desalt and purify 4-Butyrobetain from a liquid reaction mixture. The yield of 4-Butyrobetain obtained under optimized conditions was 88%.

The above described setup was also used to desalt and purify L-carnitine from a liquid reaction mixture. The yield of L-carnitine obtained under optimized conditions was 88-94%.

Example 1

Recovery of 4-Butyrobetain (CAS-Nr. 407-64-7) from ED Waste Stream

The waste stream of a commercial scale ED plant was treated in a nanofiltration pilot plant. A commercial four inch spiral wound membrane module from Kochmembranes Type TFC-SR-3 with 7.9 $m^2$ membrane area was used to concentrate 500 kg of the waste stream to 126 kg. The initial temperature was 23° C. and was adjusted to 44° C. during the experiment. The initial pressure was 14 bar and was adjusted during the experiment up to 30 bar. Samples were taken from the retentate (concentrate) and the permeate (waste water). The concentration of Butyrobetain rose from an initial 2.6 weight % to 8.4 weight %. The retention was calculated to be 80-100% during the course of the concentration phase. The retention of 4-hydroxybutanoic acid was calculated to be 30-95% during the course of the concentration phase. Sodium chloride was not retained by the membrane during the course of the experiment.

Based on the results from the nanofiltration experiment and data from the ED plant, a total mass balance was calculated. The total yield of 4-Butyrobetain can be raised significantly from 88% as shown in the Comparative Example to 98% if the nanofiltration process is used as a post-treatment of the ED waste stream and the retained product is recycled to the ED.

Example 2

Recovery of L-Carnitine (CAS-Nr. 541-15-1) from ED Waste Stream

The waste stream of the ED plant on lab scale described above was treated in a nanofiltration plant on lab scale. A membrane module filled with NittoDenko's flat sheets membrane Type NTR-729HG S4F with 0.02 $m^2$ membrane area was used to concentrate 2.648 kg of the waste stream to 0.835 kg. The temperature was 23° C. during the experiment. The pressure was 32 bar. Samples were taken from the retentate (concentrate) and the permeate (waste water). The concentration of L-carnitine in retentate rose from an initial 1.3 weight % to 3.3 weight %. The retention was calculated to be 80-100% during the course of the concentration phase. The retention of (E)-4-Hydroxycrotonic acid was calculated to be 30-95% during the course of the concentration phase. Sodium chloride was not retained by the membrane during the course of the experiment.

Based on the results from the nanofiltration experiment and data from the ED miniplant, a total mass balance was calculated. The total yield of L-carnitine can be raised significantly from 88% as shown in the Comparative Example to 98% if the nanofiltration process is used as a post-treatment of the ED waste stream and the retained product is recycled to the ED.

The invention claimed is:

1. A process for the recovery of betaines from electrodialysis waste streams from betaine production processes comprising:
    synthesizing a betaine in a reaction mixture to form a product stream;
    purifying the product stream by using an electrodialysis unit to produce a purified product stream and a waste stream;
    treating the waste stream by feeding the waste stream through a pressure driven membrane process, wherein the pressure driven membrane process comprises nanofiltration to produce a recovered product stream and a salt stream containing salts; and
    purifying the recovered product stream by feeding the recovered product stream directly to an electrodialysis unit to produce a purified recovered product stream that is combined with the purified product stream.

2. A process according to claim 1, wherein the product stream and the recovered product stream are both fed to the same electrodialysis unit.

3. A process according to claim 1, wherein the product stream and the recovered product stream are fed to different electrodialysis units.

4. The process according to claim 1, whereby said betaines are selected from the group consisting of 4-butyrobetaine and L-carnitine.

5. The process according to claim 1, whereby said waste streams contain salts.

6. The process according to claim 1, wherein the retention of betaines is in the range of 80-100%.

7. The process according to claim 1, wherein the retention of betaines is about 100%.

8. The process according to claim 1, whereby the retention of the salts is below 50%.

9. The process according to claim 1, whereby the retention of the salts is below 10%.

10. The process according to claim 1, wherein the pressure driven membrane process includes an applied membrane, the membrane comprising a polymer or a ceramic.

11. The process according to claim 1, wherein the product stream is channeled into a plurality of electrodialysis units.

12. The process according to claim 1, wherein the waste stream contains the betaine, inorganic salts, and organic compounds.

13. The process according to claim 12, wherein the inorganic salts present in the waste stream comprise sodium chloride and sodium hydroxide.

14. The process according to claim 12, wherein the organic compounds present in the waste stream comprise 4-hydroxybutanoic acid, (E)-4-hydroxycrotonic acid, and mixtures thereof.

15. The process according to claim 1, wherein the waste stream contains the betaine which is purified by treating the waste stream with the pressure driven membrane process, the recovered product stream containing the betaine which is combined with more betaine contained in the purified product stream.

* * * * *